US007138546B2

(12) United States Patent
Tang

(10) Patent No.: US 7,138,546 B2
(45) Date of Patent: Nov. 21, 2006

(54) COMPOUNDS AND COMPOSITIONS FOR DELIVERING ACTIVE AGENTS

(75) Inventor: Pingwah Tang, Elmsford, NY (US)

(73) Assignee: Emisphere Technologies, Inc., Tarrytown, NY (US)

( * ) Notice: Subject to any disclaimer, the term of this patent is extended or adjusted under 35 U.S.C. 154(b) by 0 days.

(21) Appl. No.: 10/362,067

(22) PCT Filed: Aug. 16, 2001

(86) PCT No.: PCT/US01/25679

§ 371 (c)(1),
(2), (4) Date: May 7, 2003

(87) PCT Pub. No.: WO02/16309

PCT Pub. Date: Feb. 28, 2002

(65) Prior Publication Data

US 2003/0216287 A1 Nov. 20, 2003

Related U.S. Application Data

(60) Provisional application No. 60/226,390, filed on Aug. 18, 2000.

(51) Int. Cl.
| | |
|---|---|
| C07C 235/16 | (2006.01) |
| C07C 235/18 | (2006.01) |
| A61K 38/28 | (2006.01) |
| A61K 31/165 | (2006.01) |
| A61K 31/16 | (2006.01) |
| A31K 38/23 | (2006.01) |
| A31K 31/727 | (2006.01) |

(52) U.S. Cl. ............... 564/171; 514/2; 514/3; 514/54; 514/56; 514/617; 514/622; 514/623; 514/625; 424/85.2; 424/85.4; 564/201

(58) Field of Classification Search ........... 564/175, 564/201; 514/2.3, 54, 56, 623, 625, 617, 514/622, 2, 3; 424/85.4, 85.2
See application file for complete search history.

(56) References Cited

U.S. PATENT DOCUMENTS 5,583,020 A 12/1996 Sullivan 5,863,944 A 1/1999 Leone-Bay et al.
6,358,504 B1 3/2002 Leone-Bay et al.
6,384,278 B1 5/2002 Tang et al.

FOREIGN PATENT DOCUMENTS

| JP | 48-37819 B1 | 11/1973 |
| JP | 60-126256 | * 7/1985 |
| WO | WO00/07979 | 2/2000 |
| WO | WO02/15959 | 2/2002 |

OTHER PUBLICATIONS

Yalcin at al., Synthesis and Microbiological Activity of some Novel N-(2-Hydroxyl-5-substituted Phenyl) Benzacetamides, Phenoxyacetamides and Thiophenoxyacetamides. Il Farmaco. 1997, vol. 52, No. 11, pp. 685-689, especially p. 686, compound 5a-k and p. 687, Table 1.
International Search Report dated Jan. 2, 2002.
Trapani et al., Synthesis; vol. 12 (1983), pp. 1013-1014. *
"Trimethylamine-Borane as Useful Reagent in the N-Acylation or N-Alkylation of Amines by Carboxylic Acids"; Giuseppe Trapani, Antonia Reho, Andrea Latrofa; Synthesis International Journal of Methods of Synthetic Organic Chemistry, 12:1013 (Dec. 1983).
"A Convenient Method of Amidation of Carboxlic Aids Using Boron Tifluroide Etherate"; Junichi Tani, Toyonari Oine, Ichizo Inoue; Synthesis International Journal of Methods of Synthetic Organic Chemistry, 11:714 (Nov. 1975).
"Some Amide Forming Reactions Involving Boron Reagents"; A. Pelter, T.E. Levitt and P. Nelson; Tetrahedron. vol. 26, pp. 1539-1544, Pergamon Press 1970.
"A New Synthesis of Amides and Macrocyclic Lactams"; David B. Collum, Shen-Chu Chen, Bruce Ganem, The Journal of Organic Chemistry; vol. 43, No. 22, Oct. 27, 1978.
"3,4,5-Trifluorobenzeneboronic Acid as an Extremely Active Amidation Catalyst"; The Journal of Organic Chemistry; vol. 61, No. 13, Jun. 28, 1996.
English Abstract of JP 60-126256 (Jul. 5, 1985).

* cited by examiner

Primary Examiner—Shailendra Kumar
(74) Attorney, Agent, or Firm—Darby & Darby

(57) ABSTRACT

Compounds and compositions for the delivery of active agents are provided. Methods of administration and preparation are provided as well.

38 Claims, No Drawings

COMPOUNDS AND COMPOSITIONS FOR DELIVERING ACTIVE AGENTS

This is a U.S. national phase application under 35 U.S.C. §371 of International Patent Application No. PCT/US01/25679 filed Aug. 16, 2001, and claims the benefit of U.S. Provisional Application No. 60/226,390, filed Aug. 18, 2000, which is hereby incorporated by reference. The International Application was published in English on Feb. 28, 2002 as WO 02/16309 A1 under PCT Article 21(2).

FIELD OF THE INVENTION

The present invention relates to compounds for delivering active agents, such as biologically or chemically active agents, to a target. These compounds are well suited for forming non-covalent mixtures with active agents for oral, intracolonic, pulmonary, and other routes of administration to animals. Methods for the preparation and administration of such compositions are also disclosed.

BACKGROUND OF THE INVENTION

Conventional means for delivering active agents are often severely limited by biological, chemical, and physical barriers. Typically, these barriers are imposed by the environment through which delivery occurs, the environment of the target for delivery, and/or the target itself. Biologically and chemically active agents are particularly vulnerable to such barriers.

In the delivery to animals of biologically active and chemically active pharmacological and therapeutic agents, barriers are imposed by the body. Examples of physical barriers are the skin, lipid bi-layers and various organ membranes that are relatively impermeable to certain active agents but must be traversed before reaching a target, such as the circulatory system. Chemical barriers include, but are not limited to, pH variations in the gastrointestinal (GI) tract and degrading enzymes.

These barriers are of particular significance in the design of oral delivery systems. Oral delivery of many biologically or chemically active agents would be the route of choice for administration to animals if not for biological, chemical, and physical barriers. Among the numerous agents which are not typically amenable to oral administration are biologically or chemically active peptides, such as calcitonin and insulin; polysaccharides, and in particular mucopolysaccharides including, but not limited to, heparin; heparinoids; antibiotics; and other organic substances. These agents may be rapidly rendered ineffective or destroyed in the gastrointestinal tract by acid hydrolysis, enzymes, and the like. In addition, the size and structure of macromolecular drugs may prohibit absorption.

Earlier methods for orally administering vulnerable pharmacological agents have relied on the co-administration of adjuvants (e.g., resorcinols and non-ionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation. Liposomes have also been described as drug delivery systems for insulin and heparin. However, broad spectrum use of such drug delivery systems is precluded because: (1) the systems require toxic amounts of adjuvants or inhibitors; (2) suitable low molecular weight cargos, i.e. active agents, are not available; (3) the systems exhibit poor stability and inadequate shelf life; (4) the systems are difficult to manufacture; (5) the systems fail to protect the active agent (cargo); (6) the systems adversely alter the active agent; or (7) the systems fail to allow or promote absorption of the active agent.

Proteinoid microspheres have been used to deliver pharmaceuticals. See, for example, U.S. Pat. Nos. 5,401,516; 5,443,841; and Re. 35,862. In addition, certain modified amino acids have been used to deliver pharmaceuticals. See, for example, U.S. Pat. Nos. 5,629,020; 5,643,957; 5,766, 633; 5,776,888; and 5,866,536.

More recently, a polymer has been conjugated to a modified amino acid or a derivative thereof via a linkage group to provide for polymeric delivery agents. The modified polymer may be any polymer, but preferred polymers include, but are not limited to, polyethylene glycol (PEG), and derivatives thereof. See, for example, International Patent Publication No. WO 00/40203.

However, there is still a need for simple, inexpensive delivery systems which are easily prepared and which can deliver a broad range of active agents by various routes.

SUMMARY OF THE INVENTION

The present invention provides compounds and compositions which facilitate the delivery of active agents. Delivery agent compounds of the present invention include those having the following formulas:

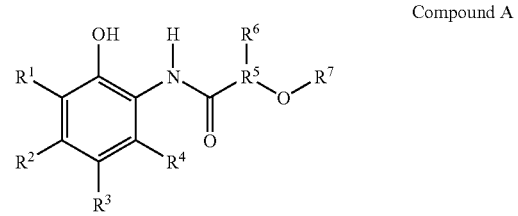

Compound A or salts thereof wherein $R^1$–$R^4$ are independently H, —OH, halogen, $C_1$–$C_4$ alkoxy, $C_1$–$C_4$ alkyl, $C_2$–$C_4$ alkenyl, $C_2$–$C_4$ alkynyl, or aryl;

$R^1$–$R^4$ are optionally substituted with halogen, —OH, $C_1$–$C_4$ alkoxy, or $C_1$–$C_4$ alkyl;

$R^5$ is a $C_1$–$C_4$ alkyl;

$R^6$ is H or $C_1$–$C_4$ alkyl;

$R^7$ is H, $C_1$–$C_4$ alkyl, or aryl; and $R^7$ is optionally substituted with halogen or —OH.

In a preferred embodiment, $R^1$–$R^4$ are independently H, halogen, or $C_1$–$C_4$ alkyl. More preferably, $R^1$–$R^4$ are independently H, Cl, or —$CH_3$.

In another preferred embodiment, $R^5$ is —$CH_3$ or —$CH_2CH_3$.

In another preferred embodiment, $R^6$ is H or —$CH_2CH_2CH_3$.

In another preferred embodiment, R is H, —$CH_2CH_3$ or aryl. More preferably, $R^7$ is 2—OH-phenyl.

In yet another preferred embodiment, the compound comprises the following or salts thereof or mixtures thereof:

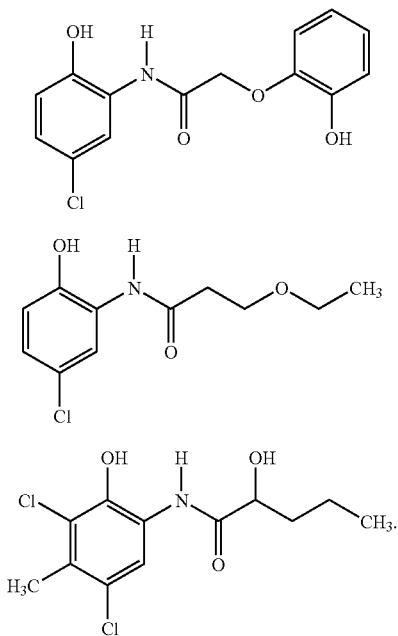

The compositions of the present invention comprise at least one active agent, preferably a biologically or chemically active agent, and at least one of the compounds, or salts thereof, of the structure of Compound A as above, including all the particular embodiments referred to above and also including Compounds 1–3. Methods for the preparation and administration of such compositions are also provided.

Also provided are dosage unit forms comprising the compositions. The dosage unit may be in the form of a liquid or a solid, such as a tablet, capsule or particle, including a powder or sachet.

Another embodiment is a method for administering an active agent to an animal in need of the active agent, by administering a composition comprising at one of the delivery agent compounds of the formulae above and the active agent to the animal. Preferred routes of administration include the oral, intracolonic and pulmonary routes.

Yet another embodiment is a method of treating a disease or for achieving a desired physiological effect in an animal by administering the composition of the present invention.

Yet another embodiment is a method of preparing a composition of the present invention by mixing at least one delivery agent compound of the formulae above, and at least one active agent.

DETAILED DESCRIPTION OF THE INVENTION

Delivery Agent Compounds

The terms "alkyl" and "alkenyl" as used herein include linear and branched alkyl and alkenyl substituents, respectively.

Each delivery agent compound may be free or in the form of a salt thereof. Suitable salts include, but are not limited to, organic and inorganic salts, for example alkali-metal salts, such as sodium, potassium and lithium; alkaline-earth metal salts, such as magnesium, calcium or barium; ammonium salts; basic amino acids, such as lysine or arginine; and organic amines, such as dimethylamine or pyridine. Preferably, the salts are sodium salts. The salts may be mono- or multi-valent salts, such as monosodium salts and di-sodium salts. The salts may also be solvates, including ethanol solvates, and hydrates.

Salts of the delivery agent compounds of the present invention may be prepared by methods known in the art. For example, sodium salts may be prepared by dissolving the delivery agent compound in ethanol and adding aqueous sodium hydroxide.

The delivery agent compounds of the present invention can be prepared as follows. A suspension of an appropriate amine (1 equivalent), an appropriate carboxylic acid (1.03 equivalent), boric acid (0.05 equivalent), and 2-amino-5-methylpyridine (0.05 equivalent) in dried toluene (concentration: 0.5 mole/L) is heated at reflux (approximately 110° C.) under nitrogen for about 4 hours during which water produced in the reaction is removed by azeotropic distillation in a Dean-Stark separation unit. Thin layer chromatography on silica gel (eluant: EtOAc/heptane: 1/1) indicates the completion of the reaction. The reaction is cooled to room temperature. The product can be isolated according to standard laboratory procedures.

The delivery agent compound may be purified by recrystallization or by fractionation on one or more solid chromatographic supports, alone or, linked in tandem. Suitable recrystallization solvent systems include, but are not limited to, ethanol, water, heptane, ethyl acetate, acetonitrile, methanol, and tetrahydrofuran and mixtures thereof. Fractionation may be performed on a suitable chromatographic support such as alumina, using methanol/n-propanol mixtures as the mobile phase; reverse phase chromatography using trifluoroacetic acid/acetonitrile mixtures as the mobile phase; and ion exchange chromatography using water or an appropriate buffer as the mobile phase. When anion exchange chromatography is performed, preferably a 0–500 mM sodium chloride gradient is employed.

The delivery agent may contain a polymer conjugated to it by a linkage group selected from the group consisting of —NHC(O)NH—, —C(O)NH—, —NHC(O), —OOC—, —COO—, —NHC(O)O—, —OC(O)NH—, —CH$_2$NH —NHCH$_2$—, —CH$_2$NHC (O)O—, —OC(O) NHCH$_2$—, —CH$_2$NHCOCH$_2$O—, —OCH$_2$C(O)NHCH$_2$—, —NHC (O)CH$_2$O—, —OCH$_2$C(O)NH—, —NH—, —O—, and carbon-carbon bond, with the proviso that the polymeric delivery agent is not a polypeptide or polyamino acid. The polymer may be any polymer including, but not limited to, alternating copolymers, block copolymers and random copolymers, which are safe for use in mammals. Preferred polymers include, but are not limited to, polyethylene; polyacrylates; polymethacrylates; poly(oxyethylene); poly (propylene); polypropylene glycol; polyethylene glycol (PEG); and derivatives thereof and combinations thereof. The molecular weight of the polymer typically ranges from about 100 to about 200,000 daltons. The molecular weight of the polymer preferably ranges from about 200 to about 10,000 daltons. In one embodiment, the molecular weight of the polymer ranges from about 200 to about 600 daltons and more preferably ranges from about 300 to about 550 daltons.

Active Agents

Active agents suitable for use in the present invention include biologically active agents and chemically active agents, including, but not limited to, pesticides, pharmacological agents, and therapeutic agents. Suitable active agents include those that are rendered less effective, ineffective or are destroyed in the gastro-intestinal tract by acid hydrolysis, enzymes and the like. Also included as suitable active agents are those macromolecular agents whose physiochemical characteristics, such as, size, structure or charge, prohibit or impede absorption when dosed orally.

For example, biologically or chemically active agents suitable for use in the present invention include, but are not limited to, proteins; polypeptides; peptides; hormones; polysaccharides, and particularly mixtures of muco-polysaccharides; carbohydrates; lipids; small polar organic molecules (i.e. polar organic molecules having a molecular weight of 500 daltons or less); other organic compounds; and particularly compounds which by themselves do not pass (or which pass only a fraction of the administered dose) through the gastro-intestinal mucosa and/or are susceptible to chemical cleavage by acids and enzymes in the gastro-intestinal tract; or any combination thereof.

Further examples include, but are not limited to, the following, including synthetic, natural or recombinant sources thereof: growth hormones, including human growth hormones (hGH), recombinant human growth hormones (rhGH), bovine growth hormones, and porcine growth hormones; growth hormone releasing hormones; growth hormone releasing factor, interferons, including α, β and γ; interleukin-1; interleukin-2; insulin, including porcine, bovine, human, and human recombinant, optionally having counter ions including zinc, sodium, calcium and ammonium; insulin-like growth factor, including IGF-1; heparin, including unfractionated heparin, heparinoids, dermatans, chondroitins, low molecular weight heparin, very low molecular weight heparin and ultra low molecular weight heparin; calcitonin, including salmon, eel, porcine and human; erythropoietin; atrial naturetic factor; antigens; monoclonal antibodies; somatostatin; protease inhibitors; adrenocorticotropin, gonadotropin releasing hormone; oxytocin; leutinizing-hormone-releasing-hormone; follicle stimulating hormone; glucocerebrosidase; thrombopoietin; filgrastim; prostaglandins; cyclosporin; vasopressin; cromolyn sodium (sodium or disodium chromoglycate); vancomycin; desferrioxamine (DFO); bisphosphonates, including alendronate, tiludronate, etidronate, clodronate, pamidronate, olpadronate, and incadronate; parathyroid hormone (PTH), including its fragments; antimicrobials, including antibiotics, anti-bacterials and anti-fungal agents; vitamins; analogs, fragments, mimetics or polyethylene glycol (PEG)-modified derivatives of these compounds; or any combination thereof. Non-limiting examples of antibiotics include gram-positive acting, bacteriocidal, lipopeptidal and cyclic peptidal antibiotics, such as daptomycin and analogs thereof.

Delivery Systems

The composition of the present invention comprises one or more delivery agent compounds of the present invention, and one or more active agents. In one embodiment, one or more of the delivery agent compounds, or salts of these compounds, or poly amino acids or peptides of which these compounds or salts form one or more of the units thereof, may be used as a delivery agent by mixing with the active agent prior to administration to form an administration composition.

The administration compositions may be in the form of a liquid. The solution medium may be water (for example, for salmon calcitonin, parathyroid hormone, and erythropoietin), 25% aqueous propylene glycol (for example, for heparin) and phosphate buffer (for example, for rhGH). Other dosing vehicles include polyethylene glycol. Dosing solutions may be prepared by mixing a solution of the delivery agent compound with a solution of the active agent, just prior to administration. Alternately, a solution of the delivery agent compound (or active agent) may be mixed with the solid form of the active agent (or delivery agent compound). The delivery agent compound and the active agent may also be mixed as dry powders. The delivery agent compound and the active agent can also be admixed during the manufacturing process.

The dosing solutions may optionally contain additives such as phosphate buffer salts, citric acid, glycols, or other dispersing agents. Stabilizing additives may be incorporated into the solution, preferably at a concentration ranging between about 0.1 and 20% (w/v).

The administration compositions may alternately be in the form of a solid, such as a tablet, capsule or particle, such as a powder or sachet. Solid dosage forms may be prepared by mixing the solid form of the delivery agent compound with the solid form of the active agent. Alternately, a solid may be obtained from a solution of the delivery agent compound and active agent by methods known in the art, such as freeze-drying (lyophilization), precipitation, crystallization and solid dispersion.

The administration compositions of the present invention may also include one or more enzyme inhibitors. Such enzyme inhibitors include, but are not limited to, compounds such as actinonin or epiactinonin and derivatives thereof. Other enzyme inhibitors include, but are not limited to, aprotinin (Trasylol) and Bowman-Birk inhibitor.

The amount of active agent used in an administration composition of the present invention is an amount effective to accomplish the purpose of the particular active agent for the target indication. The amount of active agent in the compositions typically is a pharmacologically, biologically, therapeutically, or chemically effective amount. However, the amount can be less than that amount when the composition is used in a dosage unit form because the dosage unit form may contain a plurality of delivery agent compound/active agent compositions or may contain a divided pharmacologically, biologically, therapeutically, or chemically effective amount. The total effective amount can then be administered in cumulative units containing, in total, an effective amount of the active agent.

The total amount of active agent to be used can be determined by methods known to those skilled in the art. However, because the compositions of the invention may deliver active agents more efficiently than compositions containing the active agent alone, lower amounts of biologically or chemically active agents than those used in prior dosage unit forms or delivery systems can be administered to the subject, while still achieving the same blood levels and/or therapeutic effects.

The presently disclosed delivery agent compounds facilitate the delivery of biologically and chemically active agents, particularly in oral, intranasal, sublingual, intraduodenal, subcutaneous, buccal, intracolonic, rectal, vaginal, mucosal, pulmonary, transdermal, intradermal, parenteral, intravenous, intramuscular and ocular systems, as well as traversing the blood-brain barrier.

Dosage unit forms can also include any one or combination of excipients, diluents, disintegrants, lubricants, plasticizers, colorants, flavorants, taste-masking agents, sugars, sweeteners, salts, and dosing vehicles, including, but not limited to, water, 1,2-propane diol, ethanol, olive oil, or any combination thereof.

The compounds and compositions of the subject invention are useful for administering biologically or chemically active agents to any animals, including but not limited to birds such as chickens; mammals, such as rodents, cows, pigs, dogs, cats, primates, and particularly humans; and insects.

The system is particularly advantageous for delivering chemically or biologically active agents that would otherwise be destroyed or rendered less effective by conditions encountered before the active agent reaches its target zone (i.e. the area in which the active agent of the delivery composition is to be released) and within the body of the animal to which they are administered. Particularly, the compounds and compositions of the present invention are useful in orally administering active agents, especially those that are not ordinarily orally deliverable, or those for which improved delivery is desired.

The compositions comprising the compounds and active agents have utility in the delivery of active agents to selected biological systems and in an increased or improved bioavailability of the active agent compared to administration of the active agent without the delivery agent. Delivery can be improved by delivering more active agent over a period of time, or in delivering active agent in a particular time period (such as to effect quicker or delayed delivery), or in delivering the active agent at a specific time, or over a period of time (such as sustained delivery).

Another embodiment of the present invention is a method for the treatment or prevention of a disease or for achieving a desired physiological effect, such as those listed in the table below, in an animal by administering the composition of the present invention. Specific indications for active agents can be found in the Physicians' Desk Reference (54$^{th}$ Ed., 2000, Medical Economics Company, Inc., Montvale, N.J.), which is herein incorporated by reference. The active agents in the table below include their analogs, fragments, mimetics, and polyethylene glycol-modified derivatives.

| Active Agent | Disease and Physiological Effect |
| --- | --- |
| Growth hormones | Growth disorders |
| Interferons, including α, β and γ. | Viral infection, including chronic cancer and multiple sclerosis |
| Interleukin-1; interleukin-2. | Viral infection; cancer |
| Insulin; Insulin-like growth factor IGF-1. | Diabetes |
| Heparin | Thrombosis; prevention of blood coagulation |
| Calcitonin. | Osteoporosis; diseases of the bone |
| Erythropoietin | Anemia |
| Atrial naturetic factor | Vasodilation |
| Antigens | Infection |
| Monoclonal antibodies | To prevent graft rejection; cancer |
| Somatostatin | Bleeding ulcer; erosive gastritis |
| Protease inhibitors | AIDS |
| Adrenocorticotropin | High cholesterol (to lower cholesterol) |
| Gonadotropin releasing hormone | Ovulatory disfunction (to stimulate ovulation) |
| Oxytocin | Labor disfunction (to stimulate contractions) |
| Leutinizing-hormone-releasing-hormone; follicle stimulating hormone | Regulate reproductive function |
| Glucocerebrosidase | Gaucher disease (to metabolize lipoprotein) |
| Thrombopoietin | Thrombocytopenia |
| Filgrastim | Reduce infection in chemotherapy patients |
| Prostaglandins | Hypertension |
| Cyclosporin | Transplant rejection |
| Vasopressin | Bed-wetting; antidiuretic |
| Cromolyn sodium; Vancomycin | Asthma; allergies |
| Desferrioxamine (DFO) | Iron overload |
| Parathyroid hormone (PTH), including its fragments. | Osteoporosis; Diseases of the bone |
| Antimicrobials | Infection including gram-positive bacterial infection |
| Vitamins | Vitamin deficiencies |
| Bisphosphonates | Osteoporosis; Paget's disease; Inhibits osteoclasts |

For example, one embodiment of the present invention is a method for treating a patient suffering from or susceptible to diabetes by administering insulin and at least one of the delivery agent compounds of the present invention.

Following administration, the active agent present in the composition or dosage unit form is taken up into circulation. The bioavailability of the active agent can be readily assessed by measuring a known pharmacological activity in blood, e.g. an increase in blood clotting time caused by heparin, or a decrease in circulating calcium levels caused by calcitonin. Alternately, the circulating levels of the active agent itself can be measured directly.

DESCRIPTION OF THE PREFERRED EMBODIMENTS

The following examples illustrate the invention without limitation. All parts are given by weight unless otherwise indicated.

Proton nuclear magnetic resonance ($^1$H NMR) analyses for the compounds listed below were conducted on a 300 MHz Bruker spectrometer using dimethyl sulfoxide (DMSO-d$_6$) as the solvent unless otherwise indicated.

EXAMPLE 1

Compound Preparation

Preparation of Compound 1 (N-(5-Chloro-2-hydroxyphenyl)-2-(2-hydroxyphenoxy)acetamide)

A suspension of 2 amino-4-chlorophenol (4.31 g, 30 mmol), 2-(2-hydroxyphenoxy) acetic acid (5.15 g, 30.60 mmol), boric acid (0.186 g, 3 mmol), and 2-amino-5-methylpyridine (0.326 g, 3 mmol) in 60 mL of dried toluene was heated at reflux (110° C.) under nitrogen for 16 hours, during which water (0.6 mL) produced in the reaction was removed by azeotropic distillation in a Dean-Stark separation unit. Thin layer chromatography on silica gel (eluant: EtOAc/heptane: 1/1) revealed that the reaction was complete. The reaction mixture was cooled to about room temperature, and poured into 500 mL of hexane. The slurry was stirred for about 60 minutes. The resulting solid was filtered, washed with hexane, and dried under vacuum. The solid was triturated with 100 ml of a mixture of hexane and ethyl acetate (90/10: v/v). The filtration of the mixture, followed by drying in vacuo, afforded the desired product (7.92 g, 90%) as an off-white solid. HPLC (Column: Higgins Kromasil 100 C18, water/acetonitrile/acetic acid: 950/50/1, 3 mL/min, 220 nm) Retention Time (R$_t$) 5.31 min. Melting point 203–205° C. $^1$H NMR (DMSO d$_6$, 300 MHz) δ: 4.71 (s, 2H), 6.75 (m, 1H), 6.85 (m, 2H), 6.91 (m, 2H), 7.01 (m, 2H), 8.02 (d, 1H), 9.30 (s, 1H), 9.46 (s, 1H), 10.35 (s, 1H); Karl Fischer H$_2$O content: 1.76%. Anal. Calculated for C$_{14}$H$_{12}$ClNO$_4$: C, 56.24; H, 4.24; Cl, 11.86, N, 4.69. Found: C, 56.04, H, 4.24, Cl, 11.88, N, 4.75.

Preparation of Compound 2 (N-(5-Choro-2-hydroxyphenyl)-3-ethoxypropanamide)

A suspension of 2 amino-4-chlorophenol (5.02g, 35 mmol), 3-ethoxypropanoic acid (4.22 g, 35.7 mmol), boric acid (0.108 g, 1.75 mmol), and 2-amino-5-methylpyridine (0.189 g, 1.75 mmol) in 70 mL of dried toluene was heated at reflux (110° C.) under nitrogen for 6 hours, during which water (0.65 mL) that was produced in the reaction was removed by azeotropic distillation in a Dean-Stark separation unit. Thin layer chromatography on silica gel (eluant: EtOAc/heptane: 1/1) revealed that the reaction was complete. The reaction mixture was cooled to about room temperature, and poured into 500 mL of hexane. The slurry was stirred for about 60 minutes. The resulting solid was filtered, washed with hexane, and dried under vacuum. The solid was triturated with 100 ml of a mixture of hexane and ethyl acetate (90/10 v/v). The filtration of the mixture, followed by drying in vacuo, afforded the desired product (7.79 g, 91%) as an off-white solid. HPLC (Column: Higgins Kromasil 100 C18, water/acetonitrile/acetic acid: 950/50/1, 3 mL/min, 220 nm) Retention time (R$_t$) 4.44 min. Melting Point 154–156° C. $^1$H NMR (DMSO d$_6$, 300 MHz) δ: 1.12 (t, 3H), 2.63 (t, 2H ), 3.45 (q, 2H ) 3.64 (t, 2H ), 6.85 (d, 1H ), 6.93 (dd, 1H 8.06 (d, 1H ), 9.32 (s, 1H ), 10.20 (s, 1H ). Anal. Calculated for C$_{11}$H$_{14}$ClNO$_3$: C, 54.22; H, 5.79; Cl, 14.55, N, 5.75. Found: C, 53.92; H, 5.71, Cl, 14.43, N, 5.72.

Preparation of Compound 3 (N-(3,5-dichloro-2-hydroxy-4-methylphenyl)-2-hydroxy-pentanamide)

Compound 3 was prepared by the same procedure as that for preparing Compound 2 except 6-amino-2,4-dichloro-3-methylphenol and 2-hydroxypentanoic acid were used as starting materials. The yield was 85%. HPLC (Column: Higgins Kromasil 100 C18, water/acetonitrile/acetic acid: 950/50/1, 3 mL/min, 220 nm) Retention Time (R$_t$) 5.13 min. $^1$H NMR (CHCl3, 300 MHz ) δ: 1.01 (t, 3H), 1.52 (m, 2H), 1.80–2.21 (m, 2H), 2.45 (s, 3H), 4.10 (m, 1H), 7.51 (s, 1H).

EXAMPLE 2

Salmon Calcitonin (sCT) Oral Delivery

Oral dosing (PO) compositions of delivery agent compound and salmon calcitonin (sCT) in water were prepared. Typically 450 mg of compound was added to 2.0 mL of water. Either the sodium salt of the compound was used or the free acid was converted to the sodium salt by stirring the resultant solution and adding one equivalent of sodium hydroxide (1.0 N) and diluting with water. The solution was vortexed, then heated (about 37° C.) and sonicated. The pH was adjusted to about 7 (6.5 to 8.5) with NaOH or HCl. 90 µg sCT from a stock solution was added to the solution. Water was then added to bring the total volume to about 3.0 mL (varies depending on solubility of the delivery agent compound). The final delivery agent compound dose, sCT dose and volume dose amounts are listed below in Table 1.

The typical dosing and sampling protocols were as follows. Male Sprague-Dawley rate weighing between 200–250 g were fasted for 24 hours and administered ketamine (44 mg/kg) and chlorpromazine (1.5 mg/kg) 15 minutes prior to dosing. A dosing group of five rats was administered one of the dosing solutions. For oral dosing, an 11 cm Rusch 8 French catheter was adapted to a 1 mL syringe with a pipette tip. The syringe was filled with dosing solution by drawing the solution through the catheter, which was then wiped dry. The catheter was placed down the esophagus leaving 1 cm of tubing past the rat's incisors. Solution was administered by pressing the syringe plunger.

Blood samples were collected serially from the tail artery, typically at time=0, 10, 20, 30, 60 and 90 minutes. Serum sCT was determined by testing with a EIA kit (Kit # EIAS-6003 from Peninsula Laboratories, Inc., San Carlos, Calif.) modifying the standard protocol from the kit as follows: incubated with 50 µl peptide antibody for 2 hours with shaking in the dark, washed the plate, added serum and biotinylated peptide and diluted with 4 mL buffer, and shook overnight in the dark. Numbers were adjusted according to baseline values obtained at time=0. The results from the five rats in each dosing group were averaged for each time point. The maximum is reported below in Table 1.

TABLE 1

| Oral delivery of Salmon Calcitonin (sCT) | | | | |
| --- | --- | --- | --- | --- |
| Compound | volume dose (ml/kg) | Compound Dose (mg/kg) | sCT Dose (µg/kg) | Mean Peak Serum Sct (pg/ml ± SD) (SE) |
| 1 | 1 | 150 | 30 | 49.31 ± 110.27 (49.31) |
| 2 | 1 | 150 | 30 | 126.37 ± 76.77 (34.33) |
| 2 | 1 | 150 | 30 | 19.05 ± 42.59 (19.05) |

Recombinant Human Growth Hormone (rhGH)

Oral/Intracolonic Delivery

Oral gavage (PO) and/or intracolonic (IC) dosing solutions of delivery agent compound and rhGH in phosphate buffer were prepared. A solution of the compound was made either with the sodium salt of the compound or by converting the free acid to its sodium salt. Typically, a solution of the compound was prepared in phosphate buffer and stirred, adding one equivalent of sodium hydroxide (1.0 N) when making sodium salt. The final dosing solutions were prepared by mixing the compound with an rhGH stock solution (15 mg rhGH/m made by mixing as powders 15 mg rhGH, 75 mg D-mannitol, 15 mg glycine and 3.39 mg dibasic sodium phosphate, then diluting with 2% glycerol) and diluting to the desired volume (usually 3.0 ml). The compounds and rhGH dose amounts are listed below in Table 3.

The typical dosing and sampling protocols were as follows. Male Sprague-Dawley rats weighing between 200–250 g were fasted for 24 hours and administered ketamine (44 mg/kg) and chlorpromazine (1.5 mg/kg) 15 minutes prior to dosing. A dosing group of five rats was administered one of the dosing solutions. For oral gavage (PO) dosing, an 11 cm Rusch 8 French catheter was adapted to a 1 mL syringe with a pipette tip. The syringe was filled with dosing solution by drawing the solution through the catheter, which was then wiped dry. The catheter was placed down the esophagus leaving 1 cm of tubing past the rat's incisors. Solution was administered by pressing the syringe plunger. For intracolonic (IC) dosing, a 7.5 cm Rusch catheter tube (French 8 or 6) was adapted to a syringe with an Eppendorf pipette tip. The syringe was filled with the dosing solution by drawing the solution through the catheter tube. The catheter tube was wiped dry. K-Y jelly was applied to the tip avoiding contact with the eye of the tube, and the tube was inserted into the colon through the anus until the tube was no longer visible. The solution was injected by pressing the syringe plunger, and the tube was removed.

Blood samples were collected serially from the tail artery, typically at time=0, 15, 30, 45, 60 and 90 minutes for oral and 0, 10, 20, 30, 60 and 90 for IC dosing. The five samples from each time period were pooled. Serum rHGH concentrations were quantified by an rHGH immunoassay test kit (Kit #K1F4015 from Genzyme Corporation Inc., Cambridge, Mass.). Previous studies indicated baseline values of about zero.

The maximum concentration for each group is reported below in Table 3.

TABLE 3

Oral/Intracolonic Delivery of rhGH in Rats

| Compound | Volume dose (ml/kg) | Compound Dose (mg/kg) | rhGH Dose (mg/kg) | Peak Serum [rhGH] (ng/ml) |
|---|---|---|---|---|
| 2 | 1 | 200 | 3 | 0 |

The above mentioned patents, applications, test methods, and publications are hereby incorporated by reference in their entirety.

Many variations of the present invention will suggest themselves to those skilled in the art in light of the above detailed description. All such obvious variations are within the fully intended scope of the appended claims.

What is claimed is:

1. A compound selected from the group consisting of:

Compound 1
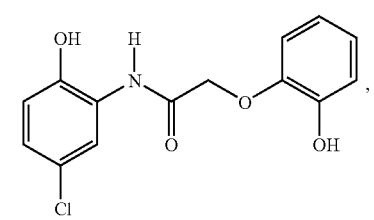

Compound 2
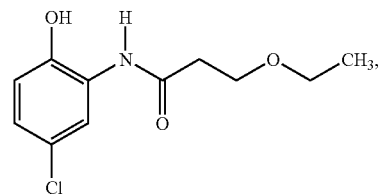

Compound 3
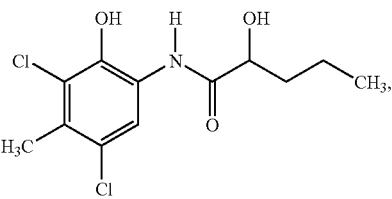

and salts thereof.

2. A composition comprising:
(A) an active agent; and
(B) a compound selected from the group consisting of Compound A
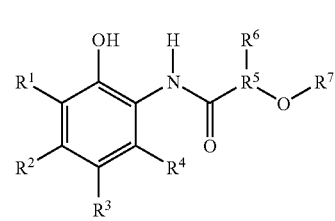

and salts thereof, and mixtures thereof.

3. The composition of claim 2, wherein the active agent is selected from the group consisting of a biologically active agent, a chemically active agent, and a combination thereof.

4. The composition of claim 3, wherein the biologically active agent comprises at least one protein, polypeptide, peptide, hormone, polysaccharide, mucopolysaccharide, carbohydrate, or lipid.

5. The composition of claim 3, wherein the biologically active agent is selected from the group consisting of:
growth hormones, human growth hormones (hGH), recombinant human growth hormones (rhGH), bovine growth hormones, porcine growth hormones, growth hormone-releasing hormones, interferons, α-interferon, β-interferon, γ-interferon, interleukin-1, interleukin-2, insulin, porcine insulin, bovine insulin, human insulin, human recombinant insulin, insulin-like growth factor (IGF), IGF-1, heparin, unfractionated heparin, heparinoids, dermatans, chondroitins, low molecular weight heparin, very low molecular weight heparin, ultra low molecular weight heparin, calcitonin, salmon calcitonin, eel calcitonin, human calcitonin; erythropoietin (EPO), atrial naturetic factor, antigens, monoclonal antibodies, somatostatin, protease inhibitors, adrenocorticotropin, gonadotropin releasing hormone, oxytocin, leutinizing-hormone-releasing-hormone, follicle stimulating hormone, glucocerebrosidase, thrombopoietin, filgrastim, prostaglandins, cyclosporin, vasopressin, cromolyn sodium, sodium chromoglycate, disodium chromoglycate, vancomycin, desferrioxamine (DFO), parathyroid hormone (PTH), fragments of PTH, antimicrobials, anti-fungal agents, vitamins; analogs, fragments, mimetics and polyethylene glycol (PEG)-modified derivatives of these compounds; and any combination thereof.

6. The composition of claim 3, wherein the biologically active agent comprises salmon calcitonin, heparin, low molecular weight heparin, hGH or combinations thereof.

7. The composition of claim 3, wherein the biologically active agent comprises salmon calcitonin.

8. A dosage unit form comprising:
(A) the composition of claim 2; and
(B) (a) an excipient,
(b) a diluent,
(c) a disintegrant,
(d) a lubricant,
(e) a plasticizer,
(f) a colorant,
(g) a dosing vehicle, or
(h) any combination thereof.

9. The dosage unit form of claim 8, wherein the active agent is selected from the group consisting of a biologically active agent, a chemically active agent, and a combination thereof.

10. The dosage unit form of claim 9, wherein the biologically active agent comprises at least one protein, polypeptide, peptide, hormone, polysaccharide, mucopolysaccharide, carbohydrate, or lipid.

11. The dosage unit form of claim 10, wherein the biologically active agent is selected from the group consisting of: growth hormones, human growth hormones (hGH), recombinant human growth hormones (rhGH), bovine growth hormones, porcine growth hormones, growth hormone-releasing hormones, interferons, α-interferon, β-interferon, γ-interferon, interleukin-1, interleukin-2, insulin, porcine insulin, bovine insulin, human insulin, human recombinant insulin, insulin-like growth factor(JGF), IGF-1, heparin, unfractionated heparin, hepannoids, dermatans, chondroitins, low molecular weight heparin, very low molecular weight heparin, ultra low molecular weight heparin, calcitonin, salmon calcitonin, eel calcitonin, human calcitonin; erythropoietin (EPO), atrial naturetic factor, antigens, monoclonal antibodies, somatostatin, protease inhibitors, adrenocorticotropin, gonadotropin releasing hormone, oxytocin, leutinizing-hormone-releasing-hormone, follicle stimulating hormone, glucocerebrosidase, thrombopoietin, filgrastim, prostaglandins, cyclosporin, vasopressin, cromolyn sodium, sodium chromoglycate, disodium chromoglycate, vancomycin, desferrioxamine (DFO), parathyroid hormone (PTH), fragments of PTH, antimicrobials, anti-fungal agents, vitamins; analogs, fragments, mimetics and polyethylene glycol (PEG)-modified derivatives of these compounds; and any combination thereof.

12. The dosage unit form of claim 10, wherein the biologically active agent comprises salmon calcitonin.

13. The dosage unit form of claim 8, wherein the dosage unit form is in the form of a tablet, a capsule, a particle, a powder, a sachet, or a liquid.

14. The dosage unit form of claim 8, wherein the dosing vehicle is a liquid selected from the group consisting of water, aqueous propylene glycol, phosphate buffer, 1,2-propane diol, ethanol, and any combination thereof.

15. A method for administering an active agent to an animal in need of the agent, the method comprising administering orally to the animal the composition of claim 2.

16. A method for preparing a composition comprising mixing:
(A) at least one active agent;
(B) the compound of claim 1; and
(C) optionally, a dosing vehicle.

17. A composition comprising:
(A) an active agent; and
(B) a compound selected from the group consisting of compounds of the formula:

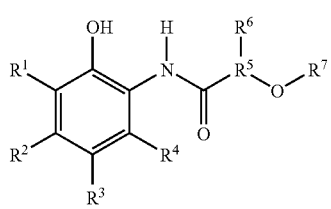

Compound A and salts thereof;
wherein:
$R^1$–$R^4$ are independently H, —OH, halogen, $C_1$–$C_4$ alkoxy, $C_1$–$C_4$ alkyl, $C_2$–$C_4$ alkenyl, $C_2$–$C_4$ alkynyl, or aryl;

$R^1$–$R^4$ are optionally substituted with halogen, -OH, $C_1$–$C_4$ alkoxy, or $C_1$–$C_4$ alkyl;
$R^5$ is a $C_1$–$C_4$ alkylene optionally substituted with a $C_1$–$C_4$ alkyl group;
$R^7$ is H, or $C_1$–$C_4$ alkyl, or aryl; and
$R^7$ is optionally substituted with halogen or —OH, and mixtures thereof.

18. The composition of claim 17, wherein the active agent comprises at least one protein, polypeptide, peptide, hormone, polysaccharide, mucopolysaccharide, carbohydrate, or lipid.

19. A compound of the formula:

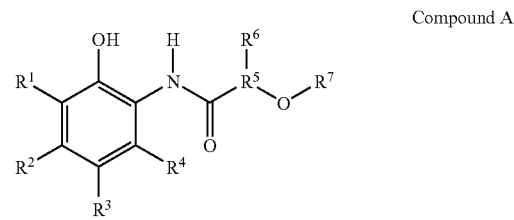

Compound A or a salt thereof
wherein:
$R^1$–$R^4$ are independently H, —OH, halogen, $C_1$–$C_4$ alkoxy, $C_1$–$C_4$ alkyl, $C_2$–$C_4$ alkenyl, $C_2$–$C_4$ alkynyl, or aryl;
$R^1$–$R^4$ are optionally substituted with halogen, —OH, $C_1$–$C_4$ alkoxy, or C1–$C_4$ alkyl;
$R^5$ is a $C_1$–$C_4$ alkylene optionally substituted with a $C_1$–$C_4$ alkyl group; and
$R^7$ is a hydroxy substituted aryl.

20. A composition comprising:
(A) an active agent; and
(B) a compound selected from the compounds of claim 19 and mixtures thereof.

21. The composition of claim 20, wherein the active agent comprises at least one protein, polypeptide, peptide, hormone, polysaccharide, mucopolysaccharide, carbohydrate, or lipid.

22. A method of administering a growth hormone comprising orally administering a composition comprising:
(a) a growth hormone; and
(b) a compound of claim 1.

23. A method of administering an interferon comprising orally administering a composition comprising:
(a) an interferon; and
(b) a compound of claim 1.

24. A method of administering interleuken-1 comprising orally administering a composition comprising:
(a) interleuken-1; and
(b) a compound of claim 1.

25. A method of administering interleuken-2 comprising orally administering a composition comprising:
(a) interleuken-2; and
(b) a compound of claim 1.

26. A method of administering heparin comprising orally administering a composition comprising:
(a) heparin; and
(b) a compound of claim 1.

27. A method of administering calcitonin comprising orally administering a composition comprising:
(a) calcitonin; and
(b) a compound of claim 1.

28. A method of administering erythropoietin comprising orally administering a composition comprising:
(a) erythropoietin; and
(b) a compound of claim 1.

29. A method of administering a monoclonal antibody comprising orally administering a composition comprising:
(a) a monoclonal antibody; and
(b) a compound of claim 1.

30. A method of administering a somatostatin comprising orally administering a composition comprising:
(a) a somatostatin; and
(b) a compound of claim 1.

31. A method of administering a protease inhibitor comprising orally administering a composition comprising:
(a) a protease inhibitor; and
(b) a compound of claim 1.

32. A method of administering a ganadotropin releasing hormone comprising orally administering a composition comprising:
(a) a ganadotropin releasing hormone; and
(b) a compound of claim 1.

33. A method of administering a leutinizing-hormone-releasing hormone comprising orally administering a composition comprising:
(a) a leutinizing-hormone-releasing hormone; and
(b) a compound of claim 1.

34. A method of administering a follicle stimulating hormone comprising orally administering a composition comprising:
(a) a follicle stimulating hormone; and
(b) a compound of claim 1.

35. A method of administering a bisphosphonate comprising orally administering a composition comprising:
(a) a bisphosphonate; and
(b) a compound of claim 1.

36. The method of claim 35, wherein the bisphosphonate is alendronate.

37. A method for administering an active agent to an animal in need of the agent, the method comprising orally administering to the animal a composition comprising the active agent and a compound of the formula:

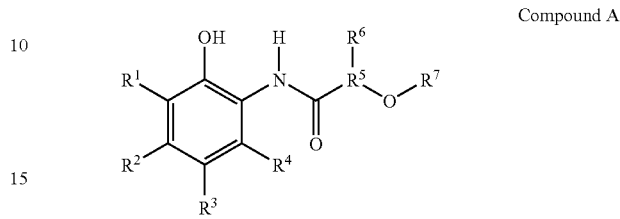

Compound A or a salt thereof,
wherein:
$R^1$–$R^4$ are independently H, —OH, halogen, $C_1$–$C_4$ alkoxy, $C_1$–$C_4$ alkyl, $C_2$–$C_4$ alkenyl, $C_2$–$C_4$ alkynyl, or aryl;
$R^1$–$R^4$ are optionally substituted with halogen, —OH, $C_1$–$C_4$ alkoxy, or $C_1$–$C_4$ alkyl;
$R^5$ is a $C_1$–$C_4$ alkylene optionally substituted with a $C_1$–$C_4$ alkyl group;
$R^7$ is H or $C_2$–$C_4$ alkyl; and
$R^7$ is optionally substituted with halogen or —OH.

38. The method of claim 37, wherein the active agent comprises at least one protein, polypeptide, peptide, hormone, polysaccharide, mucopolysaccharide, carbohydrate, or lipid.

* * * * *